DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 18, 1970

877 O.G. 489

T877,002
REACTION OF DIALKYLKETENES WITH THIOPHOSGENE

James C. Martin and Paul G. Gott, both % Tennessee Eastman Company, P.O. Box 511, Kingsport, Tenn. 77661

Continuation of application Ser. No. 686,830, Nov. 30, 1967. This application Oct. 13, 1969, Ser. No. 889,411
Int. Cl. C07c *51/58*
U.S. Cl. 260—544
No Drawing. 11 Pages Specification

Preparation of novel dialkylthiomalonyl chlorides by reacting thiophosgene with dialkylketenes of the type in which the alkyl substituents may be the same or different alkyl groups containing from 1 to 12 carbon atoms, with or without a solvent, at controlled reaction temperatures ranging from 0° to 200° C. and thereafter separating dialkylthiomalonyl chlorides thus formed from the reaction mixture by distillation. The novel compounds of the invention are useful as intermediates for the preparation of dialkylthiomalonamides, which in turn are useful as catalysts in the preparation of modified epoxy resins.